United States Patent [19]

Lalezari et al.

[11] Patent Number: 5,268,500
[45] Date of Patent: Dec. 7, 1993

[54] COMPOUND, COMPOSITION AND METHOD FOR THE REDUCTION OF LIPIDS THE MODIFICATION OF THE AFFINITY OF HEMOBLOGIN FOR OXYGEN AND THE PREVENTION OF PLATELET AGGREGATION

[75] Inventors: Iraj Lalezari, Scarsdale, N.Y.; Samuel Rahbar, Encino, Calif.; Parviz Lalezari, Scarsdale, N.Y.

[73] Assignees: Montefiore Medical Center, Bronx, N.Y.; City of Hope, Duarte, Calif.; a part interest

[21] Appl. No.: 778,706

[22] Filed: Oct. 18, 1991

Related U.S. Application Data

[63] Continuation of Ser. No. 658,096, Feb. 20, 1991, abandoned, which is a continuation of Ser. No. 515,673, Apr. 12, 1990, abandoned, which is a continuation of Ser. No. 327,020, Mar. 22, 1989, abandoned, which is a continuation of Ser. No. 62,236, Jun. 15, 1987, abandoned.

[51] Int. Cl.$^5$ .................. A61K 31/195; C07C 229/00
[52] U.S. Cl. ..................................... 560/34; 562/439
[58] Field of Search ................. 560/34; 514/564, 539; 562/439

[56] References Cited

U.S. PATENT DOCUMENTS 4,921,997  5/1990  Lalezari et al. .................. 560/34
5,093,357  3/1992  Lalezari et al. .................. 560/34

Primary Examiner—Paul J. Killos
Attorney, Agent, or Firm—Hedman, Gisbon & Costigan

[57] ABSTRACT

Novel compounds are disclosed which have the formula:

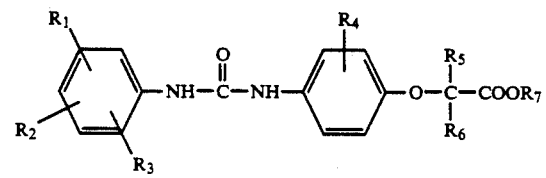

wherein $R_1$, $R_2$, $R_3$ and $R_4$ may be the same or different and independently selected from the group consisting of hydrogen, halogen, straight and branched chain alkyl of from 1-6 carbon atoms, aryl, cycloalkyl of 4 to 7 carbon atoms; and alkoxy of 1 to 6 carbon atoms; $R_5$ and $R_6$ may be the same or different and are selected from the group consisting of hydrogen, halogen, straight and branched chain alkyl groups of from 1-6 carbon atoms, aralkyl groups wherein the alkyl portion has from 1-6 carbon atoms cycloalkyl of from 4-7 carbon atoms and aryl; $R_7$ is hydrogen or a straight or branched chain alkyl group of 1-6 carbon atoms and the pharmaceutically acceptable salts thereof.

These compounds are useful for the treatment of hyperlipidemia and for the in vivo and in vitro treatment of hemoglobin or blood to modify the affinity of hemoglobin for oxygen.

13 Claims, 2 Drawing Sheets

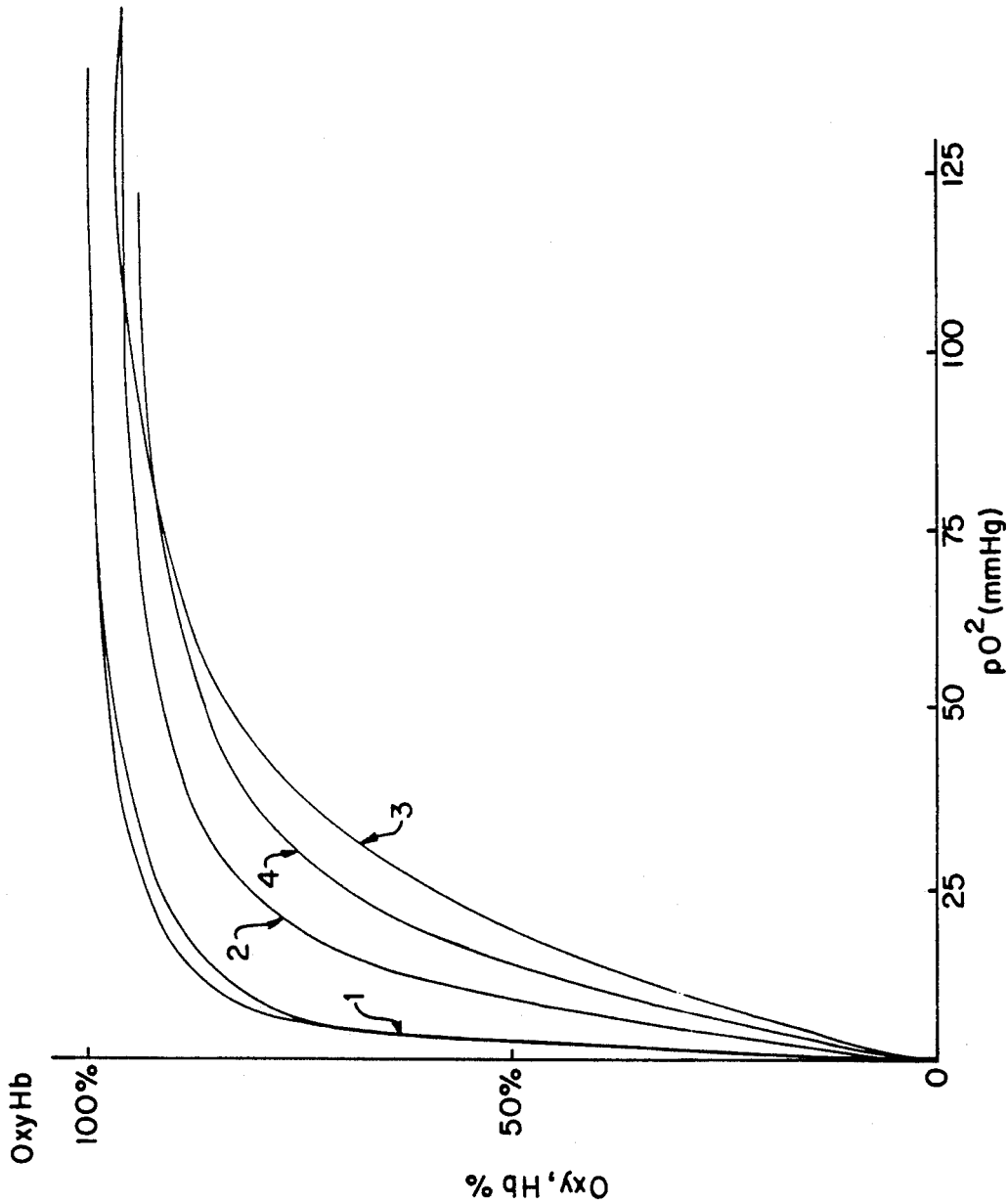

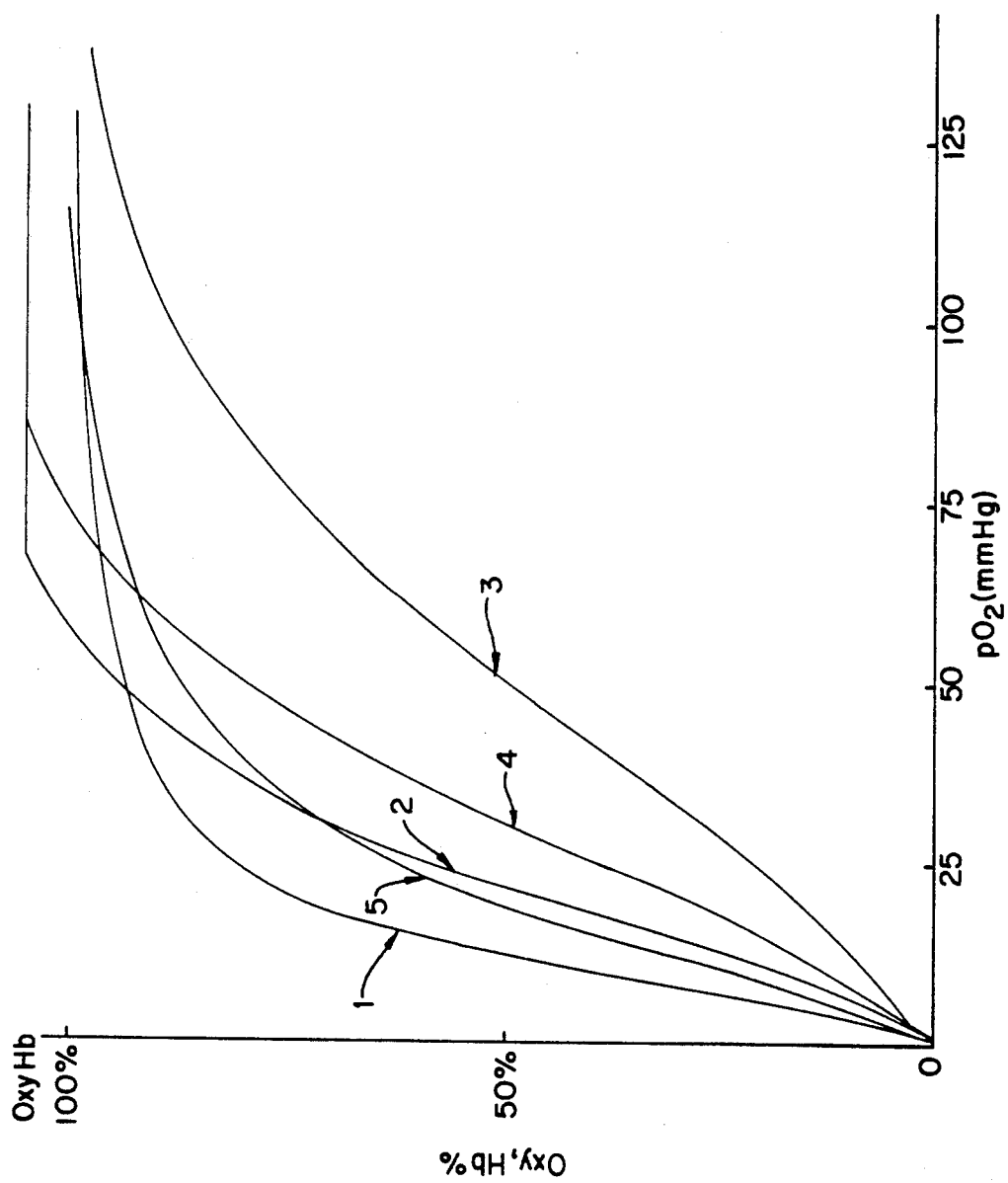

COMPOUND, COMPOSITION AND METHOD FOR THE REDUCTION OF LIPIDS THE MODIFICATION OF THE AFFINITY OF HEMOBLOGIN FOR OXYGEN AND THE PREVENTION OF PLATELET AGGREGATION

This is a continuation of application Ser. No. 07/658,096, filed Feb. 20, 1991; now abandoned which is a continuation of Ser. No. 07/515,673, filed Apr. 12, 1990, now abandoned; which is a continuation of Ser. No. 07/327,020, filed Mar. 22, 1989, now abandoned; which is a continuation of Ser. No. 07/062,236, filed Jun. 15, 1987, now abandoned.

BACKGROUND OF THE INVENTION

Many compounds have been described which are useful for the reduction of serum lipid levels. A number of these compounds are commercially available for the treatment of hyperlipidemia. Some of these compounds are disclosed in U.S. Pat. Nos. 3,781,327; 3,907,792; 3,948,973; 4,126,637; UK 860,303; UK 1,535,683; and U.S. Pat. No. 3,262,850 all of which are incorporated by references. In addition, it was known that bezafibrate, an antihyperlipoproteinemia drug was capable of lowering the oxygen affinity of hemoglobin A Perutz et al. JACS 108, 1064–1068 (1986). The compound theofibrate is known to have antilipemic, antithrombotic and platelet aggregation inhibitory activities.

The applicants have discovered a new class of phenylureido substituted phenoxy propionic acid compounds which can be administered orally to mammals to reduce total blood cholesterol levels and low density lipid-cholesterol levels without substantially affecting high density lipid-cholesterol levels. The compounds may also be utilized to modify the affinity of hemoglobin for oxygen or to prevent platelet aggregation.

Accordingly, it is a primary object of this invention to provide novel phenylureido substituted phenoxy propionic acid compounds that may be used to reduce blood lipids.

It is also an object of this invention to provide a novel pharmaceutical composition containing phenylureido substituted phenoxy propionic acid compounds.

It is also an object of this invention to provide a novel method for the treatment of hyperlipidemia in mammals which is based on the administration of a phenylureido substituted phenoxypropionic acid.

It is also an object of the invention to modify the affinity of hemoglobin for oxygen.

It is also an object of this invention to provide a method for preventing platelet aggregation.

SUMMARY OF THE INVENTION

The invention is concerned with novel compounds of the formula:

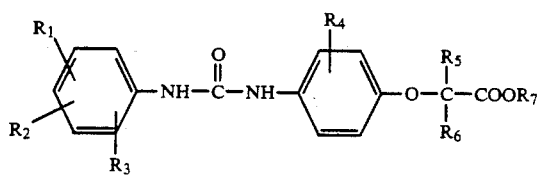

wherein $R_1$, $R_2$, $R_3$ and $R_4$ may be the same or different and independently selected from the group consisting of hydrogen, halogen, straight and branched chain alkyl of from 1-6 carbon atoms, aryl, cycloalkyl of 4 to 7 carbon atoms; and alkoxy of 1 to 6 carbon atoms; $R_5$ and $R_6$ may be the same or different and are selected from the group consisting of hydrogen, halogen, straight and branched chain alkyl groups of from 1-6 carbon atoms, aralkyl groups wherein the alkyl portion has from 1-6 carbon atoms cycloalkyl of from 4-7 carbon atoms and aryl; $R_7$ is hydrogen or a straight or branched chain alkyl group of 1-6 carbon atoms and the pharmaceutically acceptable salts thereof such as the sodium, potassium, ammonium, etc.

The invention also includes pharmaceutical compositions that are based on a compound of Formula I and methods for the reduction of hyperlipidemia by the oral administration of a compound of Formula I.

BRIEF DESCRIPTION OF THE DRAWINGS

FIG. 1 shows the effects of a compound of the invention on the oxygen dissociation of human hemoglobin solution.

FIG. 2 shows the effects of a compound of the invention on the oxygen dissociation of intact human red blood cells.

DETAILED DESCRIPTION OF THE INVENTION

The novel compounds of the invention may be prepared by the following general procedure:

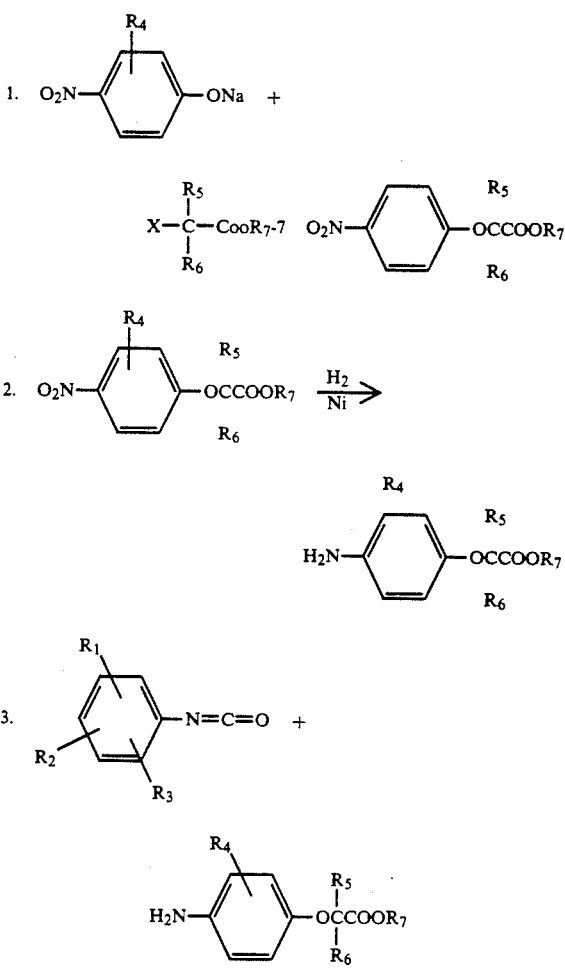

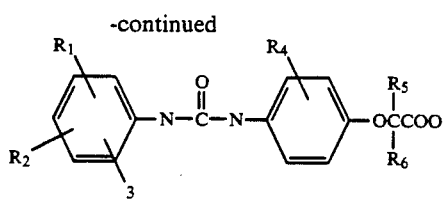

The nitrophenoxy acid is prepared according to the procedure described by P. Galimberti et al., Gazz. Chim. Ital. 77,431 (1947). The amino substituted compound is prepared by catalytic hydrogenation of the nitro compound according to the procedure of G. E. Wicks, Jr., J. Med. Chem. 15,436 (1972). The amino substituted compound is then reacted with an arylisocyanate to form the arylureido acid compound of the invention. The esters of the free acid are formed by reacting the appropriate alcohol with the free acid using conventional ester forming conditions. The pharmaceutically acceptable salts may be prepared by standard procedures using the appropriate metal or ammonium salt such as sodium hydroxide, sodium bicarbonate, potassium hydroxide and the like.

The compounds of the invention may be administered to mammals including humans to reduce or prevent hyperlipidemia especially to reduce the levels of total serum cholesterol, low density lipoprotein-associated cholesterol and triglycerides. The compounds may be administered orally at a daily dosage of from about 1 to 200 mg per kilogram of body weight and more preferably at a level of about 10 to 50 mg per kilogram of body weight. The daily dosage is to be administered as a single dose, or in divided amounts three or four times a day. It is understood that the dose may be varied according to individual sensitivity and the type of hyperlipidemia being treated. In addition the compounds may be administered parenterally or rectally. The parenteral dose will be 15–25% of the oral dosage and the rectal dosage may be adjusted to obtain the desired therapeutic affect.

The compounds of the invention may be added to whole blood or packed cells in an amount of about 50 mg to 2.0 g per unit of blood (473 ml) or unit of packed cells (235 ml) and preferably from 250 mg to 750 mg per unit of blood or unit of packed cells in order to facilitate the dissociation of oxygen from hemoglobin and improve the oxygen delivery capability of blood. When blood is stored, the hemoglobin in the blood tends to increase its affinity for oxygen by losing 2,3-diphosphoglycerides. The compounds of the invention are capable of reversing and/or preventing the functional abnormality of hemoglobin which is observed when whole blood or packed cells are stored. The compounds of the invention may be added to whole blood or red blood cell fractions in a closed system using an appropriate reservoir in which the compound is placed prior to storage or which is present in the anticoagulating solution in the blood collecting bag.

It may be desirable to administer the compound to a patient prior to and/or simultaneously with the transfusion of the treated whole blood or red cells in order to avoid substantial variations in the hemoglobin oxygen affinity due to dilution that occurs when the blood is administered.

The compounds may be administered to patients in whom the affinity of hemoglobin for oxygen is abnormally high (e.g. certain hemoglobinopathies), or when the availability of hemoglobin to tissues is decreased (e.g. in ischemic conditions such as peripheral vascular disease, coronary occlusion or cerebral vascular accidents). The compounds may also be used to inhibit platelet aggregation and may be used for antithrombotic purposes. The dosage for the modification of the affinity of hemoglobin for oxygen may be based on the dosages set forth above for hyperlipidemia and these dosages may be adjusted for parenteral use to obtain the desired therapeutic result. The compounds should not be administered to patients with sickle cell disease to avoid the possibility of excessive oxygen loss which may precipitate a sickle cell crisis.

As used herein the term halogen is used to include bromo, chloro, fluoro and iodo; the term alkyl includes straight and branched chain hydrocarbon groups of 1-6 carbon atoms such as methyl, ethyl, n-propyl, n-pentyl and the like; the term aryl includes phenyl and naphthyl; the term cycloalkyl includes cycloaliphatic groups of 4 to 7 carbon atoms such as cyclobutyl, cyclopentyl, cyclohexyl and the like; the term alkoxy is used to include $R_8OH$ groups wherein $R_8$ is alkyl of 1 to 6 carbon atoms; the term aralkyl is used to include phenalkyl groups wherein the alkyl portion is an alkylene moiety of 1-6 carbons such as benzyl, phenethyl, phenpropyl and the like.

The term pharmaceutically acceptable diluent is used to include liquid and solid materials conventionally utilized to prepare injectable dosage forms and solid dosage forms such as tablets and capsules. Water may be used for the preparation of injectable compositions which may also include conventional buffers and agents to render the injectable composition isotonic. The solid diluents and excipients include lactose, starch, conventional disintegrating agents, coatings and the like. For example, UK patent 1,535,683, which is incorporated by reference, gives several embodiments of formulation that may be utilized in the preparation of tablets and capsules.

DESCRIPTION OF THE PREFERRED EMBODIMENTS

The compounds of the invention, their preparation and use are more particularly illustrated by the following examples.

EXAMPLE 1

The nitrophenoxy 2-methyl propionic acid intermediate was prepared by the reaction of chlorofrom with 4-nitrophenol and sodium hydroxide in dry acetone as described by P. Galimberti and A. Defranceschi, Gazz. Chim. Ital. 77, 431, (1947). The yield was 54%. mp 121°–123°. (recrystallized from $CCl_4$).

The amino phenoxy hydrochloride compound was prepared by catalytic hydrogenation of the nitro compound as described by H. Z. Sommer and G. E. Wicks, Jr., J. Med. Chem. 15, 436 (1972).

The free base required for the synthesis of phenylureido derivatives was obtained by alkalinization of the hydrochloride with 1N NaOH followed by the addition of concentration acetic acid to precipitate the free acid as a crystalline compound. mp 214°–216°.

To a stirring solution of 2-(4-aminophenoxy)-2-methylpropionic acid, 0.975 g (5 mmoles) in 5 ml 1N NaOH, cooled to ice salt bath temperature, 0.543 ml (5 mmoles) of phenylisocyanate was dropwise added. Stirring continued overnight at room temperature. Water, 15 ml was added and pH adjusted to 10 by the addition of 1N NaOH. The solution was charcoaled and filtered. It was acidified with hydrochloric acid. The white precipitate was filtered, washed with water and dried. It was recrystallized from aqueous acetone (charcoaled) to colorless shining plates. mp 195°-196°. (Yield 94%).

EXAMPLE 2

To a stirred solution of 2-(4-aminophenoxy)-2-methylpropionic acid, 0.975 g (5 mmoles) in 5 ml 1N NaOH (5 mmoles) and cooled to ice bath temperature, a solution of 0.767 g 4-chlorophenylisocyanate in 10 ml tetrahydrofuran was dropwise added. Stirring continued 2 hours at room temperature. It as then diluted with 20 ml water, charcoaled, and filtered. Acidification (HCl) gave a gray powder. It was recrystallized from aqueous acetone (charcoaled) as small colorless plates. mp 222°-223°. (Yield 85%).

EXAMPLE 3

To a solution of 2-(4-aminophenoxy)-2-methylpropionic acid, 0.975 g (5 mmoles) in 5 ml 1N NaOH (5 mmoles), cooled to ice salt bath temperature, a solution of 0.94 (5 mmoles) of 3,4-dichlorophenylisocyanate in 10 ml tetrahydrofuran was dropwise added. The stirring was continued for two hours at room temperature. To the reaction product, 20 ml water was added, charcoaled and filtered. Acidification with hydrochloric acid gave a light brown crystalline compound. It was recrystallized twice (charcoaled) from aqueous acetone to give large silvery plates. mp 184-185. (Yield 80%).

All compounds prepared were checked by TLC for the purity. The structure elucidation was based on NMR and IR spectroscopy and elemental analysis.

EXAMPLE 4

FIG. 1 illustrates the oxygen dissociation curves produced by a 50 uM solution of normal human hemoglobin tested at pH 7.2 using TRIS as the buffer in a Hemox analyzer. In this test, percent oxygen saturation (on the vertical axis) is plotted against the partial pressure of oxygen ($pO^2$ in the horizontal axis). Curve #1 shows the normal oxygen dissociation curve in the absence of any modifying agent. Curve #2 shows a shift to the right when 5 mM Bezafibrate that was solubilized with an equimolar amount of sodium bicarbonate is added. Curve #3 shows the right shift caused by 1 mM concentration of the compound of Example 3 that was solubilized with an equimolar amount of sodium bicarbonate and curve #4 shows the shift affected by the presence of 0.5 mM of the compound of Example 3. FIG. 2 illustrates the same effects when the intact human RBCs are treated with the same compounds. In this example, 50 uL washed human RBCs were suspended in 4 ml of HEPES buffer (pH 7.4) and oxygen dissociation curves were obtained. Curve #1 shows the oxygen dissociation curve produced by Hb in untreated RBCs. Curve #2 illustrates the right shift caused by the presence of 5 mM Bezafibrate. The effects of 1 mM and 0.5 mM of the compound of Example 3 are shown in curves #3 and #4 respectively. Curve #5 was obtained after the RBCs that had been mixed with 1 mM of the compound of Example 3 that was solubilized with an equimolar amount of sodium bicarbonate were washed once and then retested. This example illustrates that the effect of the compound of Example 4 can be reversed by washing.

EXAMPLE 5

This example describes the cholesterol and lipoprotein reducing activities of the compounds of the invention. Three groups of Sprague Dawley rats (five in each group) and each weighing 200 g were studied. Animals in Group one received normal rat diet. Animals in Groups two and three received Nath's diet for 15 days. Nath's diet is composed of 49% sucrose, 24% coconut oil, 18% casein, vitamin mixture 2%, Maize oil 1%, Mineral salts 4%, cholic acid 1%, and cholesterol 1%. Animals in Group two received no medications and served as hyperlipemic controls. Animals in Group 3 received 30 mg/kg/day of the compound of Example 3 mixed with their food. At the end of fifteen days all the animals were sacrificed and their blood cholesterol and lipids were measured. The results are as follows:

| | Total Cholesterol | Trigly | HDL-Chol. | LDL-Cho |
|---|---|---|---|---|
| Normal Diet | 53 ± 10 | 45 ± 12 | 42 ± 13 | 5 ± 5 |
| Nath Diet | 162 ± 48 | 120 ± 41 | 72 ± 25 | 66 ± 40 |
| Nath Diet and Compound of Example 3 | 117 ± 22 | 104 ± 25 | 65 ± 31 | 32 ± 34 |

These data show significant reduction in total cholesterol and LDL-cholestrol in the compound of Example 3 treated animals despite a highly challenging lipid-rich diet.

We claim:

1. A compound of the formula:

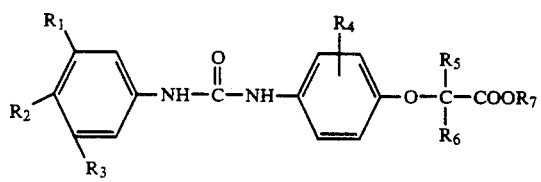

wherein $R_1$ is always hydrogen, $R_2$ is chloro or hydrogen, $R_3$ is chloro or hydrogen and $R_4$ is independently selected from the group consisting of hydrogen, halogen, straight and branched chain alkyl of from 1-6 carbon atoms, ary, cycloalkyl of 4 to 7 carbon atoms and alkoxy of 1 to 6 carbon atoms; $R_5$ and $R_6$ may be the same or different and are selected from the group consisting of hydrogen, halogen, straight and branched chain alkyl groups of from 1-6 carbon atoms, aralkyl groups wherein the alkyl portion has from 1-6 carbon atoms cycloalkyl of from 4-7 carbon atoms and aryl; $R_7$ is hydrogen or a straight or branched chain alkyl group of 1-6 carbon atoms and the pharmaceutically acceptable salts thereon.

2. A compound as defined in claim 1 which is 2-(4-(phenylureido)-phenoxy)-2-methylropionic acid.

3. A compound as defined in claim 1 which is 2-2-(4-(chlorophenylureido)phenoxy)-2-methylpropionic acid.

4. A compound as defined in claim 1 which is 2-(4-(3,4-dichlorophenylureido)phenoxy)-2-methylpropionic acid.

5. A compound as defined in claim 1 which is the sodium salt of 2-(4-(3,4-dichlorophenylureido)phenoxy)-2-methylpropionic acid.

6. A pharmaceutical composition which comprise a compound of the formula:

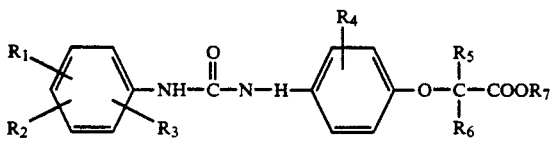
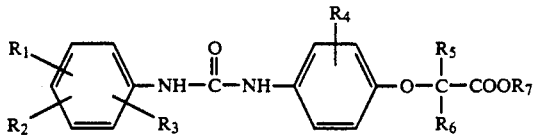

wherein $R_1$, $R_2$, $R_3$ and $R_4$ may be the same or different and independently selected from the group consisting of hydrogen, halogen, straight and branched chain alkyl of from 1-6 carbon atoms, aryl, cycloalkyl of 4 to 7 carbon atoms; and alkoxy of 1 to 6 carbon atoms; $R_5$ and $R_6$ may be the same or different and are selected from the group consisting of hydrogen, halogen, straight and branched chain alkyl groups of from 1-6 carbon atoms, aralkyl groups wherein the alkyl portion has from 1-6 carbon atoms cycloalkyl of from 4-7 carbon atoms and aryl; $R_7$ is hydrogen or a straight or branched chain alkyl group of 1-6 carbon atoms and the pharmaceutically acceptable salts thereof and a pharmaceutically acceptable diluent.

7. A pharmaceutical composition as defined in claim 6 wherein the compound is 2-(4-(phenylureido)phenoxy)-2-methylpropionic acid.

8. A pharmaceutical composition as defined in claim 6 wherein the compound is 2-(4-chlorophenylureido)-phenoxy(-2-methylpropionic acid.

9. A pharmaceutical composition as defined in claim 6 wherein the compound is 2-(4-(3,4-dichlorophenylureido)phenoxy)-2-methylpropionic acid.

10. A method for the treatment of hyperlipidemia in a mammal which comprises administering a compound of claim 1.

11. A method for treating hemoglobin or blood in vivo or in vitro to modify the affinity of hemoglobin for oxygen, said method comprising causing an effective amount of the compound of claim 1 to come in contact with hemoglobin.

12. A method for the treatment of hyperlipidemia in a mammal which comprises administering a compound of the formula:

wherein $R_1$, $R_2$, $R_3$ and $R_4$ may be the same or different and independently selected from the group consisting of hydrogen, halogen, straight and branched chain alkyl of from 1-6 carbon atoms, ary, cycloalkyl of 4 to 7 carbon atoms and alkoxy of 1 to 6 carbon atoms; $R_5$ and $R_6$ may be the same or different and are selected from the group consisting of hydrogen, halogen, straight and branched chain alkyl groups of from 1-6 carbon atoms, aralkyl groups within the alkyl portion has from 1-6 carbon atoms cycloalkyl of from 4-7 carbon atoms and aryl; $R_7$ is hydrogen or a straight or branched chain alkyl group of 1-6 carbon atoms and the pharmaceutically acceptable salts thereon.

13. A method for treating hemoglobin or blood in vivo or in vitro to modify the affinity of hemoglobin for oxygen, said method comprising causing an effective amount of the compound of the formula to come to contact with hemoglobin:

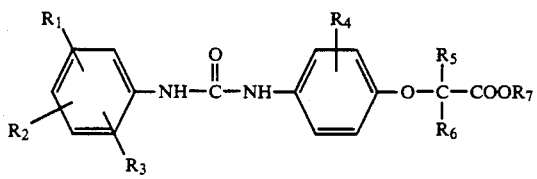

wherein $R_1$, $R_2$, $R_3$ and $R_4$ may be the same or different and independently selected from the group consisting of hydrogen, halogen, straight and branched chain alkyl of from 1-6 carbon atoms, ary, cycloalkyl of 4 to 7 carbon atoms and alkoxy of 1to 6 carbon atoms; $R_5$ and $R_6$ may be the same or different and are selected from the group consisting of hydrogen, halogen, straight and branched chain alkyl groups of from 1-6 carbon atoms, aralkyl groups wherein the alkyl portion has from 1-6 carbon atoms cycloalkyl of from 4-7 carbon atoms and aryl; $R_7$ is hydrogen or a straight or branched chain alkyl group of 1-6 carbon atoms and the pharmaceutically acceptable salts thereof.

* * * * *